US006849093B2

(12) United States Patent
Michelson

(10) Patent No.: US 6,849,093 B2
(45) Date of Patent: Feb. 1, 2005

(54) EXPANSION CONSTRAINING MEMBER ADAPTED FOR USE WITH AN EXPANDABLE INTERBODY SPINAL FUSION IMPLANT AND METHOD FOR USE THEREOF

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 201 days.

(21) Appl. No.: 10/094,467

(22) Filed: Mar. 8, 2002

(65) Prior Publication Data

US 2002/0128712 A1 Sep. 12, 2002

Related U.S. Application Data

(60) Provisional application No. 60/274,869, filed on Mar. 9, 2001.

(51) Int. Cl.[7] .................................................. A61F 2/44
(52) U.S. Cl. .................................. 623/17.15; 623/17.11
(58) Field of Search ........................... 623/17.11, 17.12, 623/17.13, 17.14, 17.15, 17.16; 606/61, 60, 63, 31, 73

(56) References Cited

U.S. PATENT DOCUMENTS

| 4,501,269 | A | * | 2/1985 | Bagby | 606/61 |
|---|---|---|---|---|---|
| 4,657,550 | A | * | 4/1987 | Daher | 623/17.11 |
| 4,763,644 | A | * | 8/1988 | Webb | 606/61 |
| 4,878,915 | A | * | 11/1989 | Brantigan | 623/17.11 |
| 5,489,308 | A | * | 2/1996 | Kuslich et al. | 623/17.11 |
| 5,980,522 | A | * | 11/1999 | Koros et al. | 606/61 |
| 6,117,174 | A | * | 9/2000 | Nolan | 623/17.11 |
| 6,344,057 | B1 | * | 2/2002 | Rabbe et al. | 623/17.11 |
| 6,436,140 | B1 | * | 8/2002 | Liu et al. | 623/17.11 |
| 6,436,142 | B1 | * | 8/2002 | Paes et al. | 623/17.15 |
| 6,440,168 | B1 | * | 8/2002 | Cauthen | 623/17.14 |
| 6,454,807 | B1 | * | 9/2002 | Jackson | 623/17.15 |
| 6,471,724 | B2 | * | 10/2002 | Zdeblick et al. | 623/17.16 |
| 6,613,091 | B1 | * | 9/2003 | Zdeblick et al. | 623/17.16 |
| 6,723,128 | B2 | * | 4/2004 | Uk | 623/17.15 |

\* cited by examiner

*Primary Examiner*—Pedro Philogene
(74) *Attorney, Agent, or Firm*—Martin & Ferraro, LLP

(57) ABSTRACT

An implant cap is disclosed for preventing the over-expansion of an expandable spinal implant and method for use therewith. An implant cap also is disclosed for moving an expandable spinal implant from a collapsed position to an expanded position with less than one full turn of the implant cap and a method for use therewith. A screw lock is disclosed for locking a bone screw to the trailing end of an expandable spinal implant and a method for use therewith.

116 Claims, 7 Drawing Sheets

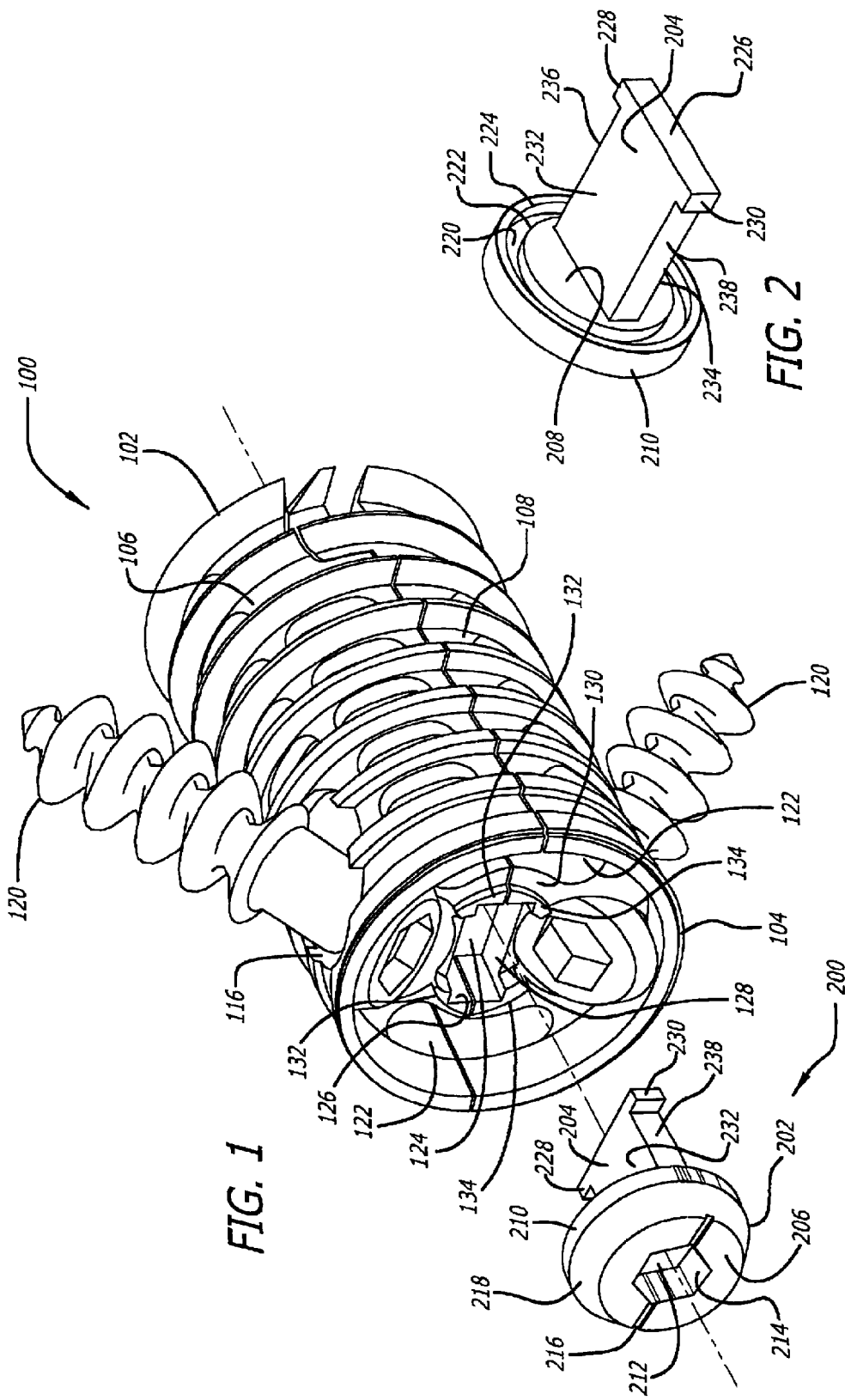

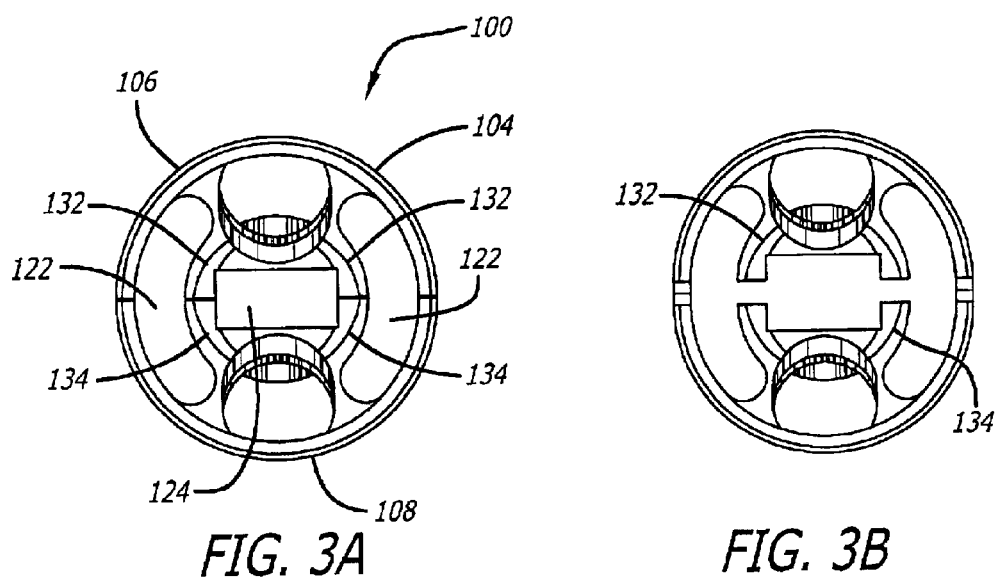
FIG. 3A
FIG. 3B
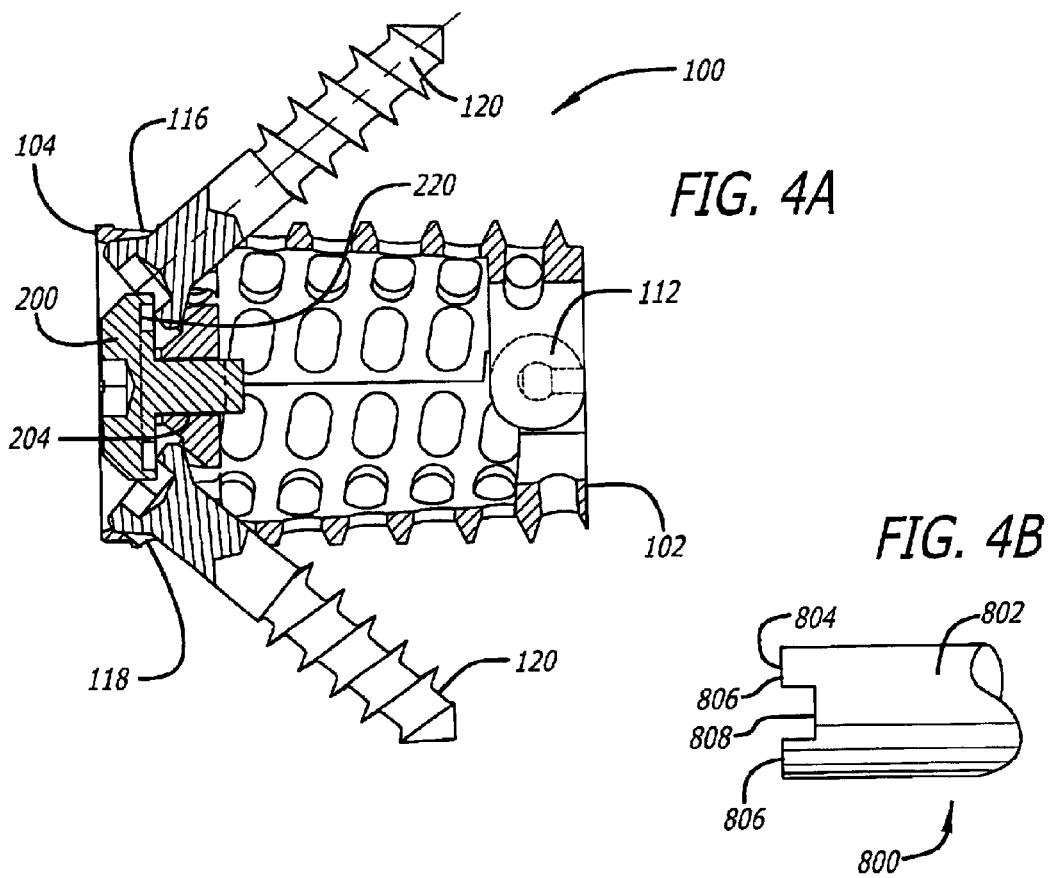
FIG. 4A
FIG. 4B

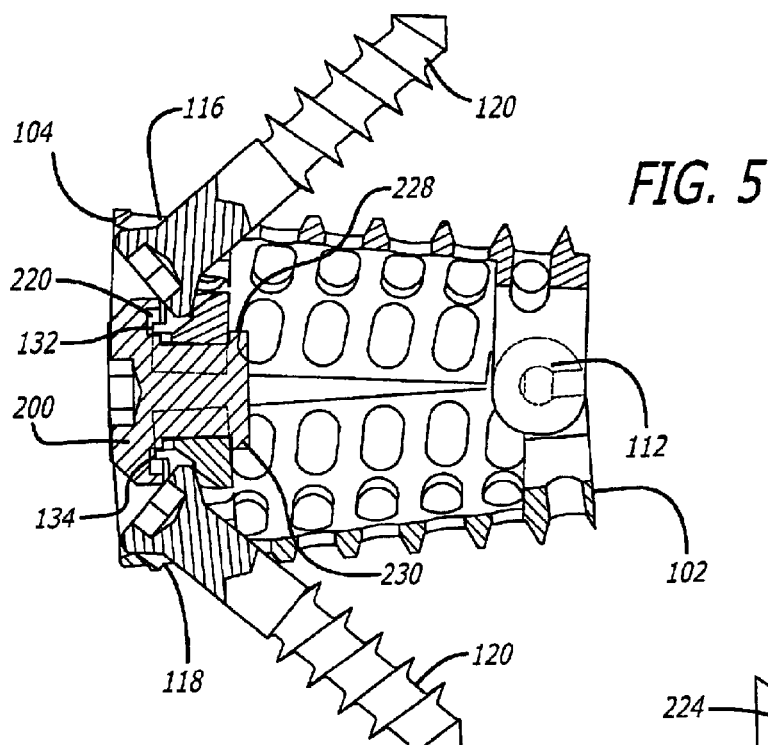
FIG. 5
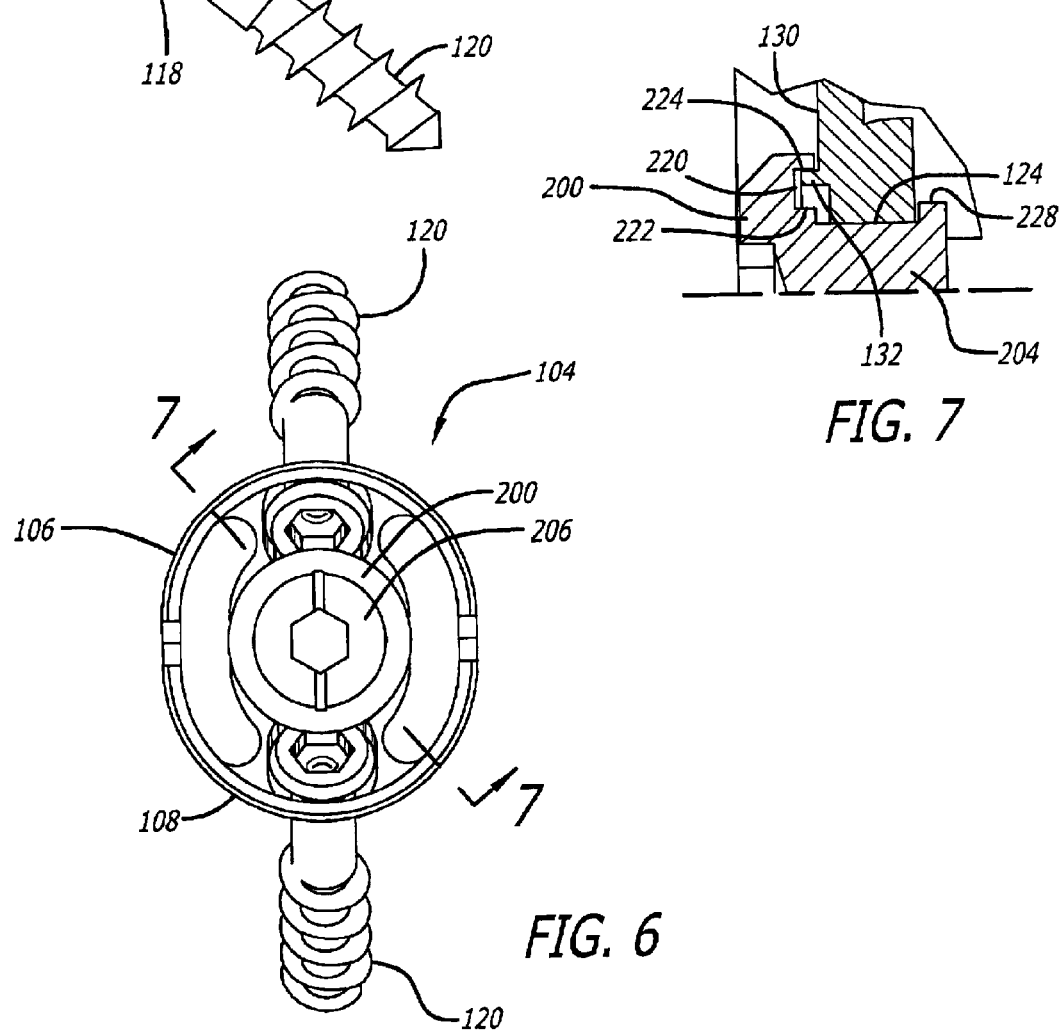
FIG. 7
FIG. 6

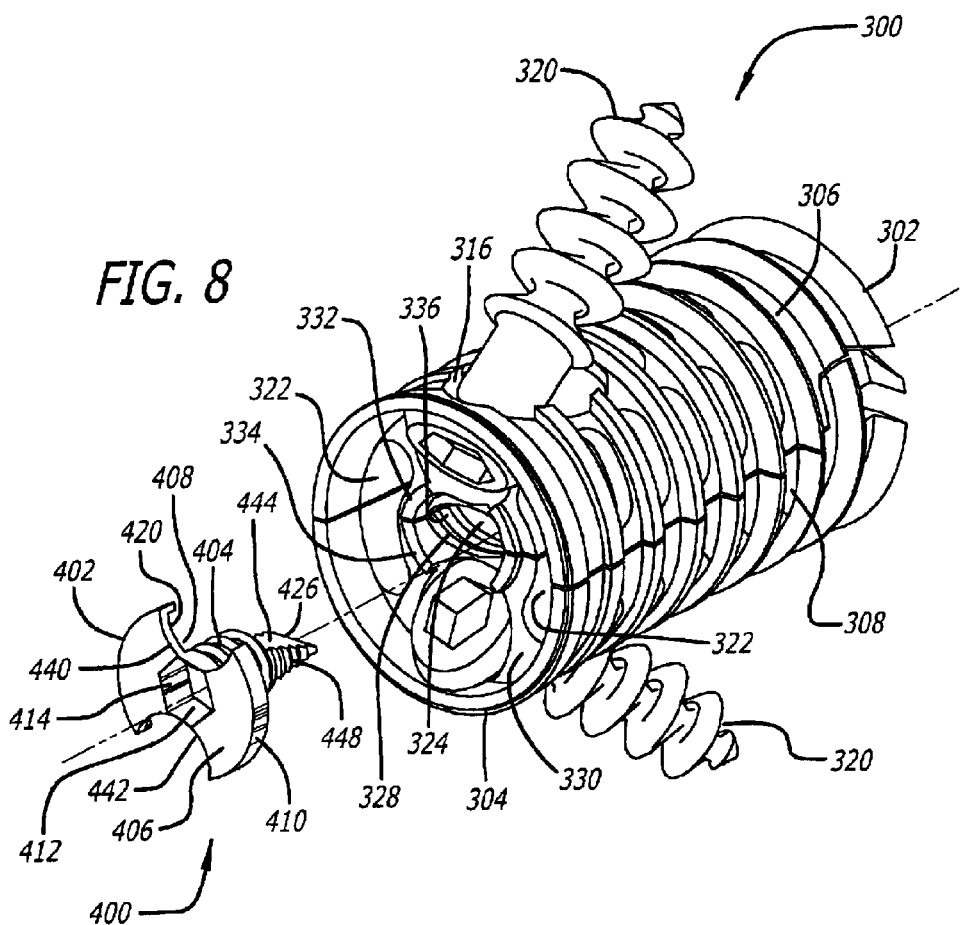

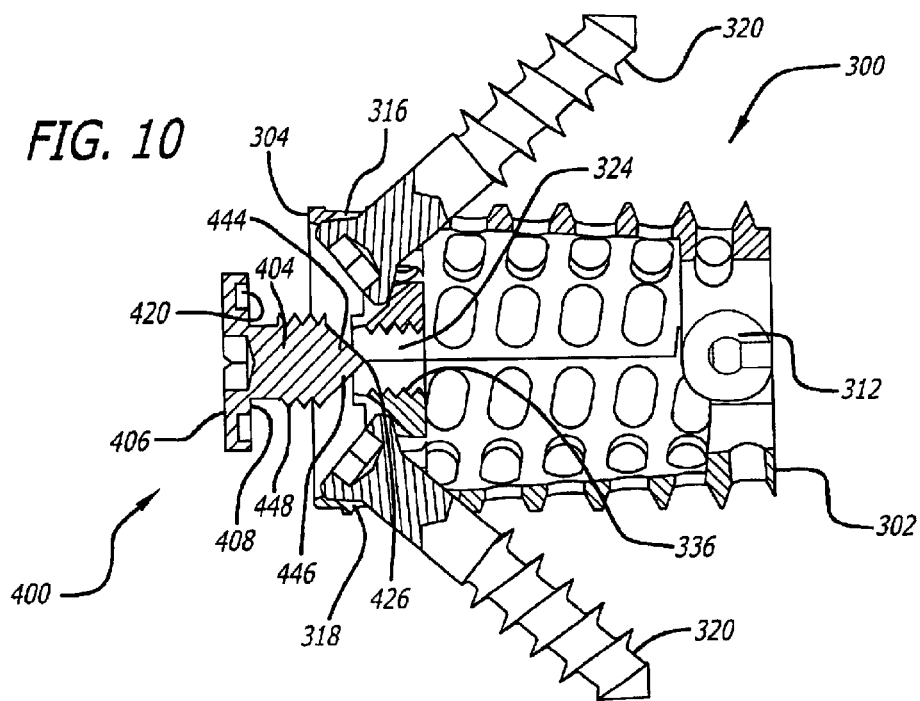
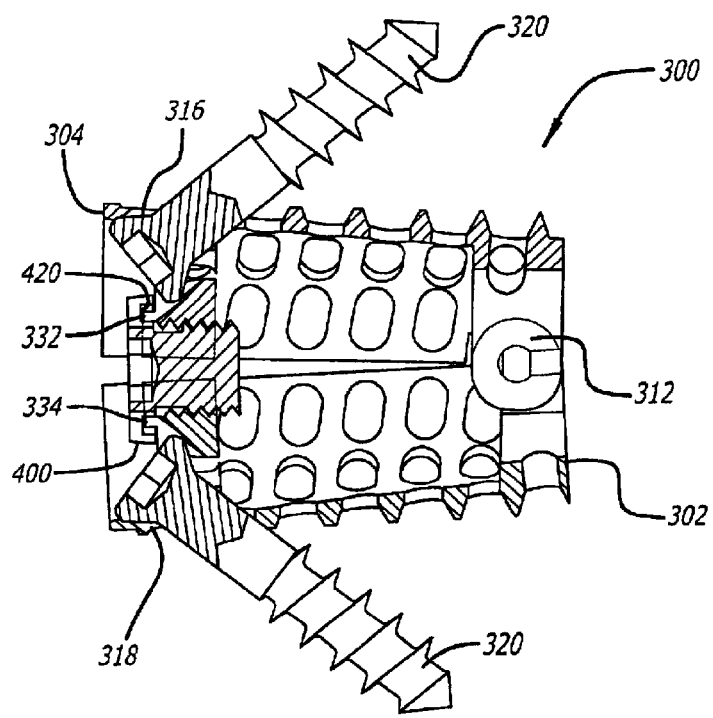

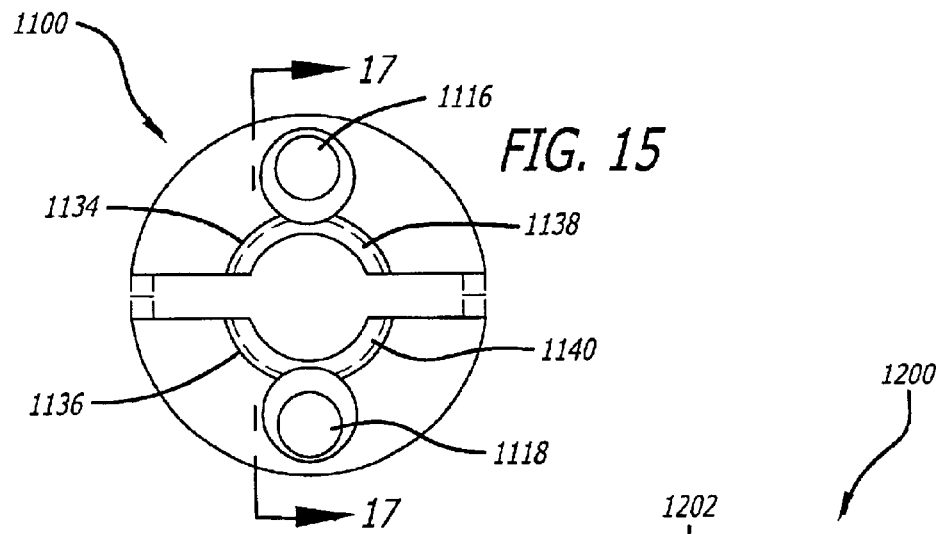
FIG. 15
FIG. 16
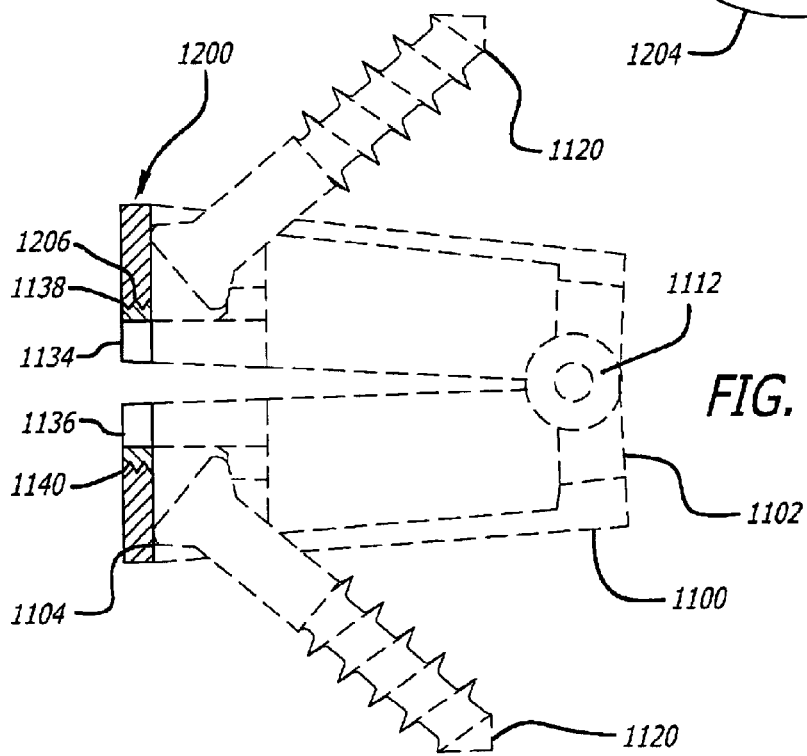
FIG. 17

EXPANSION CONSTRAINING MEMBER ADAPTED FOR USE WITH AN EXPANDABLE INTERBODY SPINAL FUSION IMPLANT AND METHOD FOR USE THEREOF

RELATED APPLICATIONS

This application claims the benefit of U.S. provisional application No. 60/274,869, filed Mar. 9, 2001, the disclosure of which is incorporated herein by reference.

BACKGROUND OF THE INVENTION

Expandable implants are known in the field of spinal surgery. Many expandable implants require complex mechanisms in order to expand the implant. Greatly simplifying the expansion of an expandable implant is a device taught by Michelson in U.S. patent application Ser. No. 09/551,964, the disclosure of which is incorporated by reference herein, that moves the implant from a collapsed position to an expanded position with less than one full turn of an expander used to expand the implant. Expandable implants often have no provision for preventing the over-expansion of the implant while the implant is being expanded in the disc space. One of the embodiments of expandable implants taught by Michelson in the '964 application utilizes a hook and peg arrangement that is integral with the implant to prevent over-expansion.

In certain circumstances, the upper and lower members of the expandable implant can move away from one another and merely securing the upper and lower members to the adjacent vertebral bodies either with vertebral body engaging projections or with bone screws is not adequate. An example of such a circumstance occurs when the surgeon elects to approach the spine anteriorly, which generally requires severing and/or removing substantial portions of the anterior longitudinal ligament over the operated area. The anterior longitudinal ligament is positioned along the anterior spinal surface and prevents hyperextension of the spine as an individual bends backward. Because the anterior longitudinal ligament covers the anterior spinal surface, the surgeon must cut through this tough ligament to access the disc space below, compromising the stability of the spine. Specifically, the anterior longitudinal ligament is generally lax, except when an individual leans backward, then the ligament acts as a tension band resisting elongation. If the anterior longitudinal ligament is damaged, there is no check on that spinal movement and the vertebral bodies may detrimentally angulate. Thus, what is needed is a simple, easy-to-use device that can either or both expand and prevent the over-expansion of an implant, and further can be used, if desired, to lock bone screws to an implant having bone screws therein.

SUMMARY OF THE INVENTION

The expansion constraining member of the present invention is capable of one or more of the following functions: (1) expands the implant by moving the upper and lower members apart, (2) maintains the implant in an expanded state by holding at least a portion of the upper and lower members apart so as to maintain the increased height of the implant and resist the collapse of the implant to the collapsed implant height, (3) prevents the implant from expanding beyond a predetermined amount by engaging at least a portion of the upper and lower members, and (4) locks bone screws to the implant by blocking the exit path of the bone screws in a direction opposite to the direction of insertion. Expansion of the implant preferably increases the implant height only, that is in a plane passing through the mid-longitudinal axis of the implant and the upper and lower members. The expansion constraining member preferably resists further expansion of the implant and makes possible vertical stability of the implant at its expandable end. The use of screws allows reconstruction of the function of the anterior longitudinal ligament. In a preferred embodiment, the expansion constraining member is capable of performing all four of the aforementioned enumerated functions.

The expansion constraining member of the present invention offers numerous advantages over devices of the prior art, a few of which include economy of parts, simplicity, and less mass occupying the interior of the implant. If the expansion constraining member is also a blocker to maintain the implant in an expandable state, an additional blocker is not needed in the implant itself. If the expansion constraining member is also an expander for expanding the implant to an expanded position, an additional expander is not needed. If the expansion constraining member is also a lock for locking the bone screws to the implant, an additional lock to lock the bone screws is not needed. An expansion constraining member capable of performing the aforementioned functions in one structure reduces the number of parts needed to perform additional functions. Further, the expansion constraining member of the present invention is preferably adapted to occupy less space of the implant interior, thereby increasing the available volume for holding fusion promoting materials in the implant.

In accordance with the purposes of the present invention, as embodied and broadly described herein, an implant cap of this invention is provided for use in expanding an expandable spinal implant having upper and lower portions adapted to move apart from one another to contact adjacent upper and lower vertebral bodies, respectively, of a human spine. The cap includes a head having a top surface and a bottom surface opposite the top surface. The head is configured to cooperatively engage an end of the implant to at least in part cover an opening in the end of the implant. The cap also includes a stem projecting from the bottom surface of the head. The stem has a distal end, opposed sides having a width therebetween, and upper and lower surfaces having a height therebetween. The width of the stem is greater than the height of the stem proximate the distal end of the stem when the cap is in an insertion position. The opposed sides are configured to move the upper and lower portions of the implant apart from one another when the cap is rotated from the insertion position to a deployed position.

In accordance with the purposes of a further embodiment of the present invention, as embodied and broadly described herein, an implant cap is provided for use in preventing the over-expansion of an expandable spinal implant having upper and lower portions adapted to move apart from one another to contact adjacent upper and lower vertebral bodies, respectively, in the human spine. The cap includes a head configured to cooperatively engage an end of the implant to at least in part cover an opening in the end of the implant. The head has a top surface and a bottom surface opposite the top surface. The bottom surface of the head of the cap has either a recess or a protrusion adapted to cooperatively engage either a protrusion or a recess, respectively, on the end of the implant to prevent the implant from expanding beyond a predetermined height. The cap also includes a stem projecting from the bottom surface of the head. The stem is adapted for insertion into the opening of the implant.

The implant cap may be part of an apparatus for insertion within an implantation space formed across the height of a disc space between vertebral bodies of a human spine. The apparatus includes an expandable spinal implant having upper and lower portions adapted to move apart from one another to contact adjacent upper and lower vertebral bodies, respectively. The implant has an end having an opening. Each of the upper and lower portions of the implant have either a recess or a protrusion to cooperatively engage either a protrusion or a recess, respectively, on the bottom surface of the cap to prevent the implant from expanding beyond a predetermined height.

In accordance with the purposes of a further embodiment of the present invention, as embodied and broadly described herein, a method of this invention is provided for engaging an end cap having a stem to an expandable spinal implant having an end. The method includes the steps of inserting the stem of the end cap into the end of the implant; rotating the stem of the end cap to expand the height of the implant; and using a portion of the end cap to prevent the implant from expanding beyond a predetermined height.

In accordance with the purposes of a further embodiment of the present invention, as embodied and broadly described herein, a method of this invention is provided for expanding an expandable spinal implant having an end. The method includes the steps of providing an end cap having a stem projecting therefrom; inserting at least a portion of the stem of the end cap into the end of the implant while the implant is in a collapsed position; and rotating the stem of the end cap less than one full turn to expand the implant from the collapsed position to an expanded position.

The accompanying drawings, which are incorporated in and constitute a part of this specification, are by way of example only and not limitation, and illustrate several embodiments of the invention, which together with the description, serve to explain the principles of the invention. The scope of the invention is limited only by the scope of the claims as from the present teachings other embodiments of the present invention shall be apparent to those skilled in the art.

BRIEF DESCRIPTION OF THE DRAWINGS

FIG. 1 is an exploded trailing end perspective view of an expandable interbody spinal fusion implant with an expanding and constraining member in the form of an end cap for expanding the implant, blocking an opening to the implant, restraining over-expansion of the implant, and locking bone screws to the implant in accordance with a preferred embodiment of the present invention;

FIG. 2 is a leading end perspective view of the end cap of FIG. 1;

FIG. 3A is a trailing end elevation view of the implant of FIG. 1 in a collapsed state;

FIG. 3B is a trailing end elevation view of the implant of FIG. 1 in an expanded state;

FIG. 4A is a side elevation view in partial cross section of the implant of FIG. 1 in an unexpaded state and with the end cap inserted therein;

FIG. 4B is a fragmentary side elevation view of an expander tool for expanding an expandable interbody spinal fusion implant from a posterior approach to the spine;

FIG. 5 is a side elevation view in partial cross section of the implant of FIG. 1 in an expanded state and with the end cap inserted therein;

FIG. 6 is a trailing end elevation view of the implant of FIG. 1 in an expanded state with the end cap inserted and in the locked position;

FIG. 7 is a fragmentary cross sectional side elevation view along line 7—7 of the implant of FIG. 6 showing a lip portion of the implant trailing end against the outer perimeter of a recess in the end cap for preventing over-expansion of the implant;

FIG. 8 is a trailing end perspective view of an expandable interbody spinal fusion implant with an expanding and constraining end cap for expanding the implant, blocking an opening to the implant, restraining over-expansion of the implant, and locking bone screws to the implant in accordance with another preferred embodiment of the present invention;

FIG. 9 is a trailing end elevation view of the implant of FIG. 8;

FIG. 10 is a side elevation view in partial cross section of the implant of FIG. 8 in an unexpanded state and with the end cap being inserted therein;

FIG. 11 is a side elevation view in partial cross section of the implant of FIG. 8 in an expanded state with the end cap inserted therein;

FIG. 15 is a trailing end elevation view of an expandable interbody spinal fusion implant in accordance with another preferred embodiment of the present invention;

FIG. 16 is a trailing end elevation view of an expansion constraining member in the form of a constraining ring for restraining over-expansion of the implant of FIG. 15 in accordance with another preferred embodiment of the present invention; and FIG. 17 is a side elevation view in partial cross section and hidden line of the implant of FIG. 15 in an expanded state and with the constraining ring of FIG. 16 installed.

DETAILED DESCRIPTION OF THE DRAWINGS

Figure 12:
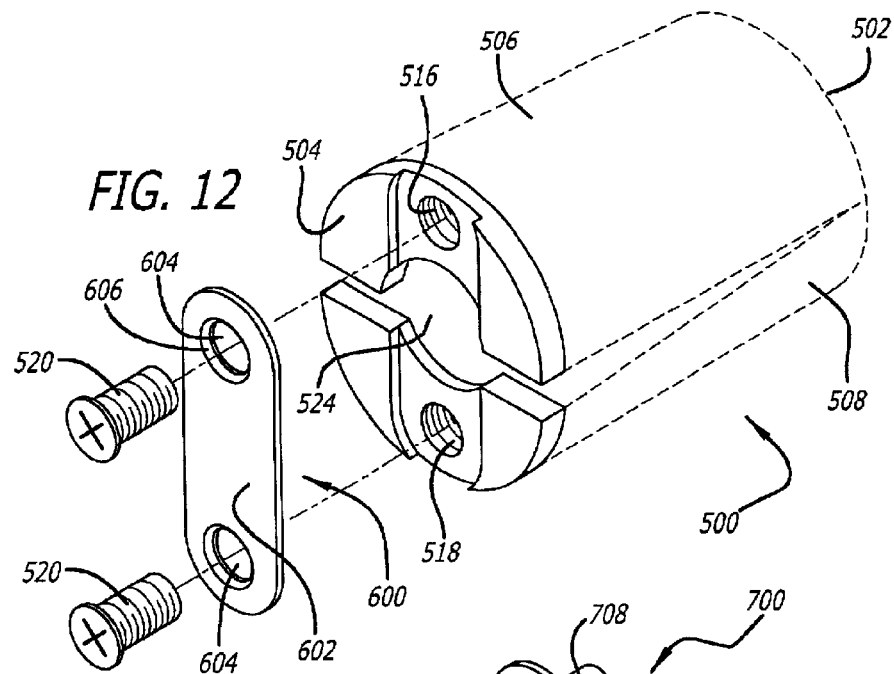
FIG. 12 is a trailing end perspective view of an expandable interbody spinal fusion implant and an end member for constraining over-expansion of the implant in accordance with another preferred embodiment of the present invention.

Reference will now be made in detail to the present preferred embodiments (exemplary embodiments) of the invention, examples of which are illustrated in the accompanying drawings.

The expansion constraining member of the present invention is adapted for use with expandable interbody spinal fusion implants. To better understand the structure and interrelationship of the expansion constraining member and the expandable interbody spinal fusion implant, the structure and associated characteristics for one embodiment of an implant adapted to be used with the expansion constraining member of the present invention will be described first.

FIGS. 1–7 show a preferred embodiment of an expandable interbody spinal fusion implant 100 and an expansion constraining end cap 200 for use therewith in accordance with the present invention. The expansion constraining member of the present invention is not limited for use with implant 100 and may be used with other expandable interbody spinal fusion implants such as, but not limited to, those taught by Michelson in WIPO Publication No. 01/56513, entitled "Expandable Impacted Interbody Spinal Fusion Implant," U.S. patent application Ser. No. 09/612,188, entitled "Expandable Push-In Arcuate Interbody Spinal Fusion Implant with Cylindrical Configuration During Insertion," U.S. patent application Ser. No. 09/551,964, entitled "Expandable Threaded Arcuate Interbody Spinal Fusion Implant with Cylindrical Configuration During Insertion," U.S. patent application Ser. No. 09/574,858, entitled "Expandable Threaded Arcuate Interbody Spinal Fusion Implant with Lordotic Configuration During Insertion," U.S. patent application Ser. No. 09/772,309, entitled "Expandable Push-In Arcuate Interbody Spinal Fusion Implant with Tapered Configuration During Insertion," the disclosures of which are incorporated by reference herein, As shown in FIGS. 1, 3A, and 3B, implant 100 has a leading end 102, a trailing end 104, an upper member 106, and a lower member 108. Upper and lower members 106, 108 are each preferably arcuate at least in part and adapted for placement toward and at least in part within the upper and lower of two adjacent vertebral bodies, respectively. Upper and lower members 106,108 preferably include at least one opening adapted to communicate with one of the adjacent vertebral bodies, the openings being in communication with one another and adapted for permitting for the growth of bone from adjacent vertebral body to adjacent vertebral body through the implant. Upper and lower portions 106,108 also preferably define a hollow interior therebetween for holding bone growth promoting material, the hollow interior preferably being in communication with the openings in upper and lower portions 106, 108. Trailing end 104 of implant 100 preferably includes openings 122 to permit for the packing of additional fusion promoting substances into the implant after the implant expansion and the application of the locking member, and to permit for the growth of bone through implant 100.

As shown in FIGS. 4 and 5, upper and lower members 106, 108 are moveable relative to one another and have a first position that allows for a collapsed implant height and a second position that allows for an increased height. Upper and lower members 106, 108 are preferably articulated at an articulation point proximate leading end 102 of implant 100. Upper and lower members 106, 108 are articulated to one another at a pivot point 112 so one of the respective ends of upper and lower members 106, 108 remain articulated while the other of the respective ends of upper and lower members 106, 108 are free to move away from one another. The cooperating rotational articulation 112 preferably is proximate one of the proximal end and the distal end of upper and lower members 106, 108 at an end opposite to an end cap 200. Other types of articulation as would be known to one of ordinary skill in the art are within the scope of the present invention.

Upper and lower members 106, 108 preferably have an upper screw hole 116 and a lower screw hole 118, respectively passing therethrough, each adapted to receive a bone screw 120 passing from the interior of implant 100 into an adjacent vertebral body to anchor implant 100 to an adjacent vertebral body. Bone screws are not essential to the operation of the implant, but are preferable for providing added securement of the implant to the adjacent vertebral bodies.

In certain circumstances, upper and lower members 106, 108 can move away from one another and merely securing upper and lower members 106, 108 to the adjacent vertebral bodies with bone screws is not adequate. An example of such a circumstance occurs when the surgeon elects to approach the spine anteriorly, which generally requires severing and/or removing substantial portions of the anterior longitudinal ligament over the operated area. The anterior longitudinal ligament is positioned along the anterior spinal surface and prevents hyperextension of the spine as an individual bends backward. Because the anterior longitudinal ligament covers the anterior spinal surface, the surgeon must cut through this tough ligament to access the disc space below, compromising the stability of the spine. Specifically, the anterior longitudinal ligament is generally lax, except when an individual leans backward, then the ligament acts as a tension band resisting elongation. If the anterior longitudinal ligament is damaged, there is no check on that spinal movement and the vertebral bodies may detrimentally angulate. Thus, a mechanism is needed to prevent movement of the upper and lower members relative to one another beyond a predetermined amount.

The expansion constraining member of the present invention is capable of one or more of the following functions: (1) expands the implant by moving the upper and lower members apart, (2) maintains the implant in an expanded state by holding at least a portion of the upper and lower members apart so as to maintain the increased height of the implant and resist the collapse of the implant to the collapsed implant height, (3) prevents the implant from expanding beyond a predetermined amount by engaging at least a portion of the upper and lower members, and (4) locks bone screws to the implant by blocking the exit path of the bone screws in a direction opposite to the direction of insertion. Expansion of the implant preferably increases the implant height only, that is in a plane passing through the mid-longitudinal axis of the implant and the upper and lower members. The expansion constraining member preferably resists further expansion of the implant and makes possible vertical stability of the implant at its expandable end. The use of screws allows reconstruction of the function of the anterior longitudinal ligament. In a preferred embodiment, the expansion constraining member is capable of performing all four of the aforementioned enumerated functions.

The expansion constraining member of the present invention offers numerous advantages over devices of the prior art, a few of which include economy of parts, simplicity, and less mass occupying the interior of the implant. If the expansion constraining member is also a blocker to maintain the implant in an expandable state, an additional blocker is not needed in the implant itself. If the expansion constraining member is also an expander for expanding the implant to an expanded position, an additional expander is not needed. If the expansion constraining member is also a lock for locking the bone screws to the implant, an additional lock to lock the bone screws is not needed. An expansion constraining member capable of performing the aforementioned functions in one structure reduces the number of parts needed to perform additional functions. Further, the expansion constraining member of the present invention is preferably adapted to occupy less space of the implant interior, thereby increasing the available volume for holding fusion promoting materials in the implant.

As shown in FIGS. 1, 3A, and 3B, trailing end 104 also preferably has an opening 124 adapted to engage end cap 200 and may also provide access to the interior of implant 100 for the purpose of introducing bone growth promoting materials therein. Upper and lower interior surfaces 126, 128 of opening 124 preferably have a portion that extends beyond exterior trailing end surface 130, forming upper lip portions 132 and lower lip portions 134, respectively. Upper and lower lip portions 132, 134 can be arcs of a circle such that in the expanded state, the arcs would be part of the same circle. For example, when implant 100 is in an unexpanded state, the profile of upper and lower lip portions 132, 134 preferably form the shape of at least a portion of an oval as shown in FIG. 3A. In the expanded state of implant 100, the profile of upper and lower lip portions 132, 134 preferably becomes less oval and generally more circular in shape as shown in FIG. 3B.

Cap 200 preferably has a head 202 and a stem 204. Head 202 has a perimeter preferably sized and shaped to cover at least a portion of upper and lower bone screw holes 116, 118 so as to lock bone screws 120 to implant 100. Preferably, the perimeter of head 202 has at least one arcuate portion. Head 202 has a top surface 206, a bottom surface 208, and a rim 210. Top surface 206 has a tool engagement area 212 that is preferably adapted to cooperatively engage an insertion tool. Tool engagement area 212 preferably includes a hex-shaped recess 214 adapted to engage the end of a correspondingly-shaped tool. A groove or marking 216 allows the surgeon to visually confirm the orientation of end 204 when hidden from view. Other shapes are possible for tool engagement area 212 depending upon the type of insertion tool used with the present invention, all of which are within the broad scope of the present invention.

Top surface 206 of cap 200 preferably has a bevel 218 extending around the perimeter thereof to form a reduced profile. Top surface 206 may have any shape suitable for its intended purpose though it is preferable that cap 206 generally not extend from trailing end 104 so as to avoid any undesired contact with delicate vascular and/or neurological structures adjacent thereto after implant 100 is installed in the spine.

As shown in FIG. 2, bottom surface 208 of cap 200 has a recess 220 proximate the perimeter of bottom surface 208 that is adapted to interact with upper and lower lip portions 132, 134 of implant 100. As described in further detail below, the interaction of lip portions 132, 143 and recess 120 limits any unwanted expansion or over-expansion of implant 100 beyond a predetermined height. Recess 220 has an inner perimeter 222, an outer perimeter 224, and a width therebetween adapted to accommodate the profiles of at least a portion of upper and lower lips 132, 134 of implant 100 in both an unexpanded and expanded state. The surface of outer perimeter 224 forms a flange that acts as a stop against which upper and lower lip portions 132, 134 of implant 100 are prevented from further movement away from the mid-longitudinal axis of implant 100 when implant 100 and cap 200 are engaged, as will be described in more detail below.

Stem 204 of cap 200 projects from bottom surface 208 and is sized and shaped to cooperatively engage opening 124 in trailing end 104 to expand implant 100 and to maintain implant 100 in an expanded state. Stem 204 preferably has a distal end 226 with tabs 228, 230, an upper surface 232, a lower surface 234 opposite to upper surface 232, and sides 236, 238. Tabs 228, 230 are configured to engage the interior surface of trailing end 104 such that when properly positioned within opening 124, tabs 228, 230 prevent cap 200 from backing out of opening 124 and lock cap 200 to implant 100.

Sides 236, 238 of stem 204 are configured to cooperatively engage upper and lower interior surfaces 126, 128 of opening 124. Opening 124 may have any shape suitable for its intended purpose for interacting with stem 204. For example, sides 236, 238 may be beveled or rounded to accommodate rotational contact with upper and lower interior surfaces 126, 128. Stem 204 may have a generally rectangular cross-section or a generally circular cross-section along at least a portion of the length of the stem. Stem 204 may also have a cross-section with sides 236, 238 intersecting the upper and the lower surfaces 232, 234 at junctions, which may be two diametrically opposed corners and two diametrically opposed arcs. The two diametrically opposed arcs may be each of the same radius and, preferably, the diagonal or modified hypotenuse between the opposed arcs has a maximum dimension that generally approximates the distance between the upper and lower surfaces 232, 234 such that when stem 204 is rotated from a first insertion position toward a second/deployed position, no substantial over-distraction occurs between the adjacent vertebral bodies as would occur if the height of the implant were to be increased markedly beyond that obtained in the second/deployed position. The two diametrically opposed corners may form a 90-degree angle. Additionally, sides 236, 238 may be configured to be divergent away from distal end 226 to better accommodate engagement with upper and lower interior surfaces 126, 128 while implant 100 is in the expanded state.

FIGS. 4–6 show a preferred expansion of implant 100 by cap 200. In FIG. 4, stem 204 of cap 200 is inserted through opening 124 in trailing end 104 of implant 100. After stem 204 is inserted into opening 124, tabs 228, 230 extend beyond upper and lower interior surfaces 126, 128 of opening 124 and into the interior of implant 100. Upper and lower surfaces 232, 234 of stem 204 are oriented toward upper and lower interior surfaces 126, 128 of opening 124, respectively, such that implant 100 is in a collapsed state. As cap 200 is rotated approximately 90° in either direction, sides 236, 238 of stem 204 cooperatively engage with upper and lower interior surfaces 126, 128 of opening 124, forcing apart upper and lower members 106, 108 away from the mid-longitudinal axis of implant 100 to position implant 100 in an expanded state. The configuration of stem 204 permits implant 100 to be expanded to a maximum implant height with less than one full turn. The rotation of cap 200 moves upper and lower members 106, 108 from a generally parallel orientation shown in FIG. 4 to an angled orientation shown in FIG. 5 to expand or increase the height of implant 100. During expansion of implant 100, upper and lower lip portions 132, 134 move within recess 220 of cap 200 until stem 204 ceases moving upper and lower interior surfaces 126, 128 away from the mid-longitudinal axis of implant 100. Tabs 228, 230 move into cooperative engagement with an interior portion of upper and lower members 106, 108 to lock cap 200 to implant 100 as well as lock implant 100 in an expanded state. A means to stop rotation of cap 200 when expansion is completed and secured to implant 200 may be employed. It is also within the broad scope of the present invention that cap 200 may be used to expand the implant from a first, collapsed lesser angled orientation to a second, expanded and more angled orientation.

For posterior spinal surgery, cap 200 may be preinstalled at the leading end of a posterior interbody spinal fusion implant. As shown in FIG. 4B, by way of example and not limitation, an expander tool 800 may be used to cooperatively engage the stem of cap 200 from an opening in the implant trailing end. Expander tool 800 has a shaft 802 and a distal end 804. Distal end 804 has a pair of prongs 806 and a recess 808 therebetween. Prongs 806 and recess 808 cooperate with the stem of cap 200 to rotate cap 200 and to move the implant from a collapsed state to an expanded state.

FIG. 7 shows a partial cross-section along line 7—7 of FIG. 6. As shown in FIG. 7, the maximum expansion of upper member 106 is reached when upper lip portions 132 are blocked from further motion away from the mid-longitudinal axis of implant 100 upon reaching outer perimeter 224 of recess 220. Although not shown in FIG. 7, lower lip portions 134 similarly contact outer perimeter 224 of recess 220. In this manner, expansion of implant 100 beyond a predetermined amount is prevented. Tabs 228, 230 of stem 204 bear against the interior of implant 100 and prevent removal of end cap 200 from opening 124. In the deployed position, end cap 200 locks implant 100 in an expanded state, and is itself secured from inadvertent dislodgement.

As shown in FIGS. 8–11, another preferred embodiment of the implant and end cap of the present invention is shown and generally referred to by the reference numbers 300 and 400, respectively. Implant 300 is similar to implant 100, except that opening 324 of implant trailing end 304 preferably has at least one thread 336 for cooperatively engaging with a threaded stem 404 of cap 400.

Cap 400 is similar to cap 200, except for differences noted below. Head 402 has a perimeter including an upper cutout portion 440 and a lower cutout portion 442, each being adapted to allow the passage of a bone screw 320 into implant 300 after cap 400 has been attached to implant 300. Once bone screws 320 are inserted, cap 200 may be rotated such that at least a portion of head 402 covers each of screws 320. Upper and lower cutout portions 440, 442 allow the surgeon the option of inserting bone screws 320 before or after attachment of cap 400 with implant 300.

Stem 404 has at least one thread 448 along the mid-longitudinal axis of cap 400 for cooperatively engaging with threaded opening 324 of implant 300. Distal end 426 of stem 404 has an upper surface 444 and a lower surface 446 that are at least in part tapered or convergent towards distal end 426 for assisting in the insertion of stem 404 into opening 324 of implant 300.

As shown in FIGS. 10 and 11, cap 400 is inserted into trailing end 304 of implant 300, preferably by aligning the edge of distal end 426 with the plane separating upper and lower members 306, 308. Once upper and lower surfaces 444, 446 of distal end 426 are sufficiently within threaded opening 324 of implant trailing end 304, cap 400 is rotated to allow stem thread 448 of cap 400 to cooperatively engage with threaded opening 324. The engagement of stem thread 448 with threaded opening 324 spreads apart upper and lower members 306, 308 at least along a portion of the length of implant 300. Continued rotation of cap 400 forces upper and lower lip portions 332, 334 to contact recess 420 of cap 400. The pitch of thread 448 is preferably such that as upper and lower lip portions 332, 334 reach recess 420, they come into contact with at least a portion of the outer perimeter of recess 420. Upon contact with recess 420, upper and lower lip portions 332, 334 are prevented from further movement away from the mid-longitudinal axis of implant 300. Cap 400 makes possible the full insertion of the bone screws either before or after the implant is expanded.

Those skilled in the art will appreciate that although it is preferred to use a cap to prevent over-expansion of an expandable implant, the invention is not so limited. For example, the implant trailing end may be adapted to have lip portions along the trailing end interior surface for cooperatively engaging with a recess and/or flange to prevent over-expansion of the implant. In such an instance, an over-expansion inhibiting surface may operate without a stem and/or head by relying on additional surface features of the implant trailing end, for example, a key-way entry along the opening leading to the interior lip portions or a circumferential barrier beyond the interior lip portions for preventing the over-expansion surface from traveling too far into the implant interior. It should also be apparent to those skilled in the art that the expander implant cap of the present invention may be adapted for use with a wide variety of expandable spinal implants, for example only, threaded cylindrical or frustoconical implants and impacted, push-in implants of various cross sectional shapes.

Figure 13:
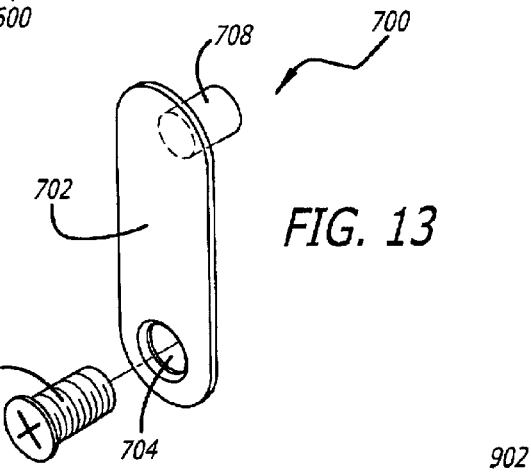
FIG. 13 is a trailing end perspective view of an end member for constraining over-expansion of the implant in accordance with another preferred embodiment of the present invention.

In other preferred embodiments, the expansion constraining member of the present invention need not be in the form of a cap. For example, FIGS. 12 and 13 show other preferred embodiments of expansion constraining member for constraining expansion of an implant 500. Implant 500 has upper and lower screw holes 516, 518 adapted to receive screws 520 to secure an expansion constraining member 600 to implant 500.

Expansion constraining member 600 preferably has a bar 602 and two openings 604. Screw openings 604 have an inner surface 606 adapted to accommodate screws 520 to lock expansion constraining member 600 to implant 500. Inner surface 606 may be threaded or smooth. Those of ordinary skill in the art will appreciate that bar 602 may be of any shape suitable for the intended purpose of restraining the over-expansion of implant 500.

Bar 602 may be planar or non-planar depending upon the orientation of the central axis of each of upper and lower screw holes 516, 518 in relation to the plane of upper and lower members 506, 508. For example, bar 602 may be non-planar to accommodate implant 500 in an expanded state while aligning screw holes 604 with upper and lower screw holes 516, 518 of implant 500 when upper and lower screw holes 516, 518 each have a central axis generally parallel to the plane of upper and lower members 506, 508, respectively. Further, upper and lower screw openings 516, 518 of implant 500 may have a central axis that is angled with respect to the plane of each of upper and lower members 506, 508 of implant 500 so that screws 520 may assist in anchoring implant 500, as with screws 120 and implant 100.

After implant 500 is moved to its second, expanded state the surgeon positions bar 602 at trailing end 504 of implant 500 and aligns screw holes 604 with each of upper and lower screw holes 516, 518. Screws 520 are inserted to lock bar 602 to implant 500.

In FIG. 13, another preferred embodiment of the expansion constraining member of the present invention is shown and generally referred to by the reference number 700. Expansion constraining member 700 is similar to expansion constraining member 600 except it has a peg 708 extending therefrom instead of a screw. A screw is passed through screw hole 704 to secure bar 702 to an implant.

Figure 14:
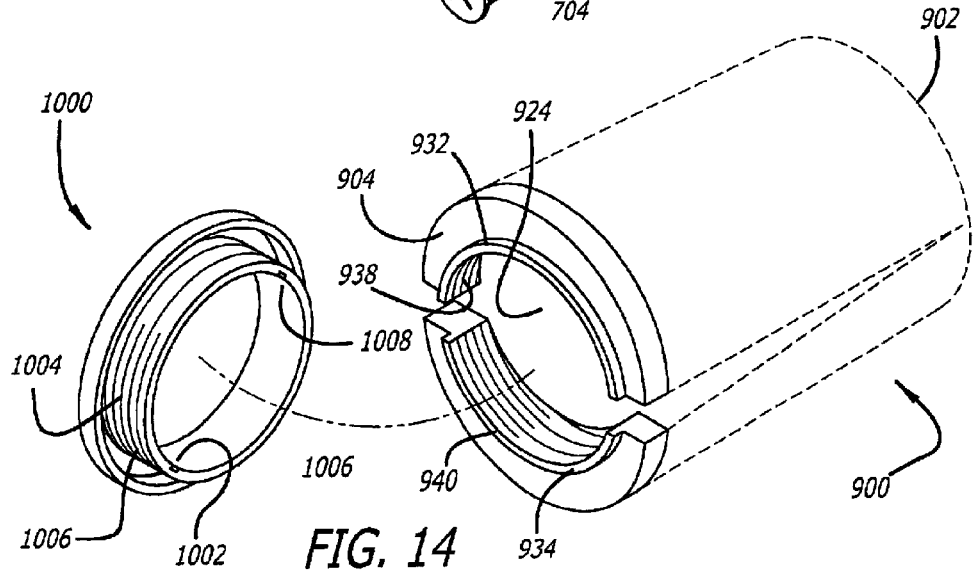
FIG. 14 is a trailing end perspective view of an expandable interbody spinal fusion implant with an expansion constraining member in the form of a constraining ring for restraining over-expansion of the implant in accordance with another preferred embodiment of the present invention.

FIG. 14 shows an implant 900 and expansion constraining member in the form of a ring 1000. Implant 900 is similar to implant 500 except that opening 924 has upper and lower lip portions 932, 934. Lip portions 932, 934 differ from those described in relation to implants 100 and 300 in that upper lip portion 932 has a thread 938 on the interior surface thereof, and lower lip portion 934 has a thread 940 on the interior surface thereof. Threads 938, 940 are adapted to mate with a thread 1006 of constraining ring 1000, described below.

Constraining ring 1000 has an inner surface 1002 and an outer surface 1004. Outer surface 1004 has thread 1006 adapted to mate with threads 938, 940 of implant 900. Inner surface 1002 has a tool engagement area 1008 adapted to cooperatively engage a tool for attaching constraining ring 1000 to implant 900. Constraining ring 1000 may be adapted to lock bone screws to implant 900 in a similar fashion as described in relation to implants 100 and 300.

Implant 900 may be expanded to its second, expanded state. Thereafter constraining ring 1000 may be inserted into opening 924 of implant 900 and screwed around the inner perimeter of upper and lower lip portions 932, 934. While these later embodiments are shown in relationship to the trailing end of the implant without bone screws that has been done for simplicity and these and other means can be adapted to serve the purpose of locking the bone screws.

FIGS. 15–17 show an implant 1100 and expansion constraining member in the form of a ring 1200. Implant 1100 is similar to implant 900 except that lip portions 1132, 1134 differ from those described in relation to implant 900 in that upper lip portion 1132 and lower lip portion 1134 have a thread portion 1138, 1140 respectively, on the exterior surface thereof. Implant 1100 also has upper and lower screw holes 1116, 1118 that are adapted to receive bone screws 1120 in a similar fashion as described in relation to implants 100 and 300.

Constraining ring 1200 is similar to constraining ring 1000 except that inner surface 1202 has thread 1206 adapted to mate with threads 1138, 1140 of implant 1100. Outer surface 1204 may have a tool engagement area adapted to cooperatively engage a tool for attaching constraining ring 1200 to implant 1100.

Implant 1100 may be expanded to its second, expanded state. Thereafter, constraining ring 1200 is attached to implant 1100 by screwing ring 1200 around the outer perimeter of upper and lower lip portions 1133, 1134 to lock bone screws 1120 to implant 1100 and constrain the over-expansion of implant 1100 as shown in FIG. 17.

The expandable spinal implant and expander implant cap may be made of artificial or naturally occurring material suitable for implantation in the human spine. The implant and/or cap may comprise at least in part bone, metal including, but not limited to, titanium and its alloys, surgical grade plastics, plastic composites, ceramics, or any other material suitable for the intended purpose. The material may be bioresorbable.

The expandable spinal implant and/or cap of the present invention may be coated with, treated with, comprised of, be used in combination with, or have a hollow for containing bone growth promoting materials and/or substances, including but not limited to, bone, bone derived products, demineralized bone matrix, ossifying proteins, bone morphogenetic proteins, hydroxyapatite, and genes coding for the production of bone. The spinal implant and/or cap of the present invention can be formed of a material that intrinsically participates in the growth of bone from one of adjacent vertebral bodies to the other of adjacent vertebral bodies, can be a source of osteogenesis, or can be at least in part bioabsorbable or resorbable. The implant and/or cap of the present invention can be formed of a porous material.

At least one of the implant and cap of the present invention may be modified, or used in combination with materials to make it antimicrobial or antibacterial, such as, but not limited to, electroplating or plasma spraying with silver ions or other substance. The expandable spinal implant and/or cap of the present invention may be coated with, comprised of, be used in combination with, or have a hollow for containing one or more chemical substances and/or compounds adapted to inhibit scar formation.

While various embodiments of the present invention are presented by way of example only and not limitation, common to each of them, is that the expandable spinal implant for insertion across the disc space between two adjacent vertebral bodies of a human spine has surface features adapted to cooperatively engage with a recess of an attachable piece for inhibiting over-expansion of the implant.

There is disclosed in the above description and the drawings caps, a lock, expansion constraining members, expanders, and implants, which fully and effectively accomplish the objectives of this invention. However, it will be apparent that variations and modifications of the disclosed embodiments may be made without departing from the principles or the scope of the present invention.

What is claimed is:

1. An implant cap movable between an insertion position for insertion into an expandable spinal implant and a deployed position for expanding the implant, the implant having upper and lower portions adapted to move apart from one another to contact adjacent upper and lower vertebral bodies, respectively, and an end with an opening configured to cooperatively receive at least a portion of said cap, said cap comprising:
a head having a top surface and a bottom surface opposite said top surface, said heed being configured to cooperatively engage the end of the implant to at least in part cover the opening in the end of the implant; and
a stem projecting from said bottom surface of said head, said stem having a distal end, opposed sides having a width therebetween, and upper and lower surfaces having a height therebetween, the width of said stem being greater than the height of said stem proximate said distal end of said stem when said cap is in the insertion position, said opposed sides being configured to move the upper and lower portions of the implant apart from one another when said cap is rotated from the insertion position to the deployed position.

2. The cap of claim 1, wherein said head is configured to cooperatively engage the end of the implant to completely cover the opening.

3. The cap of claim 1, wherein said opposed sides of said stem are beveled.

4. The cap of claim 1, wherein said opposed sides of said stem are rounded.

5. The cap of claim 4, wherein said opposed sides include a thread adapted for cooperative engagement with the implant.

6. The cap of claim 1, wherein said upper and lower surface of said stem are at least in part tapered towards said distal end of said stem.

7. The cap of claim 1, wherein said stem has a rectangular cross section along at least a portion of the length of said stem.

8. The cap of claim 1, wherein said stem has an arcuate cross section along at least a portion of the length of said stem.

9. The cap of claim 1, wherein said stem has a circular cross section along at least a portion of the length of said stem.

10. The cap of claim 1, wherein said head has a perimeter having at least one arcuate portion.

11. The cap of claim 1, wherein said distal end of said stem is adapted to cooperatively engage one of the upper and lower portions to lock said cap to the implant while the implant is in an expanded position.

12. The cap of claim 11, wherein said distal end of said stem as projections to cooperatively engage the upper and lower portions of the implant.

13. The cap of claim 1, wherein said bottom surface of said head has at least one recess and each of the upper and lower portions proximate the end of the implant has at least one protrusion, each recess being adapted to engage with at least one of the protrusions to prevent the implant from expanding beyond a predetermined height when the implant is expanded.

14. The cap of claim 1, wherein the implant has a plurality of bone screw holes, said bottom surface of said head being configured to cover at least a portion of one of the bone screw holes when said cap is engaged to the implant.

15. The cap of claim 14, wherein said bottom surface of said head is configured to cover a portion of more than one of the bone screw holes when said cap is engaged to the implant.

16. The cap of claim 14, wherein said head is configured to allow the insertion of a bone screw into the implant after said cap is engaged with the implant.

17. The cap of claim 14, wherein said head has a perimeter that is configured to permit the insertion of a bone screw into one of the bone screw holes after said cap is engaged with the implant, said head being movable to cover at least a portion of the bone screw after the bone screw is inserted in one of the bone screw holes.

18. The cap of claim 1, wherein said head is adapted to cooperatively engage a tool for attaching said cap to the implant.

19. The cap of claim 18, wherein said top surface of said head further comprises a marking to indicate the orientation of said cap to the implant once said cap is engaged to the implant.

20. The cap of claim 1, wherein said cap is treated with a bone growth promoting substance.

21. The cap of claim 1, wherein said cap comprises at least one of the following materials: metal, titanium, plastic, and ceramic appropriate for implantation in the human body.

22. The cap of claim 1, wherein said cap is at least in part resorbable.

23. The cap of claim 1, wherein said cap is formed of a porous material.

24. The cap of claim 1, in combination with a material adapted to inhibit scar formation.

25. The cap of claim 1, in combination with an antimicrobial material.

26. The cap of claim 1, in combination with a spinal implant having upper and lower portions adapted to move apart from one another to contact the vertebral bodies and an end with an opening configured to cooperatively receive at least a portion of said cap.

27. The cap of claim 26, wherein said upper and lower portions a of said implant include at least one opening adapted to communicate with one of the adjacent vertebral bodies, said openings in said upper and lower portions being in communication with one another and adapted for permitting for the growth of bone from adjacent vertebral body to adjacent vertebral body through said implant.

28. The cap of claim 27, wherein said implant includes a hollow interior for holding bone growth promoting material, said hollow interior being in communication with at least one openings in each of said upper an lower portions.

29. The cap of claim 26, wherein said implant is in combination with a bone growth promoting material.

30. The cap of claim 29, wherein said bone growth promoting material is selected from one of bone, bone derived products, demineralized bone matrix, ossifying proteins, bone morphogenetic protein, hydroxyapatite, and genes coding for the production of bone.

31. The cap of claim 26, wherein said implant is treated with bone growth promoting substance.

32. The cap of claim 26, wherein said implant comprises at least one of the following materials: metal, titanium, plastic, and ceramic appropriate for implantation in the human body.

33. The cap of claim 26, wherein said implant is at lest in part resorbable.

34. The cap of claim 26, wherein said implant is formed of a porous material.

35. The cap of claim 26, wherein said implant is in combination with a material adapted to inhibit scar formation.

36. The cap of claim 26, wherein said implant is in combination with an antimicrobial material.

37. An implant cap for preventing the over-expansion of an expandable spinal implant having upper and lower portions adapted to move apart from one another to contact adjacent upper and lower vertebral bodies, respectively, and an nd having an opening configured to cooperatively receive at least a portion of said cap, each of the upper and lower portions proximate the end of the implant having at least one protrusion, said cap comprising:

a head configured to cooperatively engage the end of the implant to at least in part cover the opening, said head having a top surface and a bottom surface opposite said top surface, said bottom surface having a recess adapted to cooperatively receive the protrusions to prevent the implant from expanding beyond a predetermined height by limiting movement of the protrusions apart from one another; and a stem projecting from said bottom surface of said head, said stem being adapted for insertion into the opening of the implant.

38. The cap of claim 37, wherein said head is configured to cooperatively engage the end of the implant to completely cover the opening.

39. The cap of claim 37, wherein the implant has a plurality of bone screw holes, said bottom surface of said head being configured to cover at least a portion of one of the bone screw holes when said cap is engaged to the implant.

40. The cap of claim 39, wherein said bottom surface of said head is configured to cover a portion of more than one of the bone screw holes when said cap is engaged to the implant.

41. The cap of claim 39, wherein said head is configured to allow the insertion of a bone screw into the implant after said cap is engaged with the implant.

42. The cap of claim 39, wherein said head has a perimeter that is configured to permit the insertion of a bone screw into one of the bone screw holes after said cap is engaged with the implant, said head being movable to cover at least a portion of the bone screw after the bone screw is inserted in one of the bone screw holes.

43. The cap of claim 37, wherein said cap is treated with a bone growth promoting substance.

44. The cap of claim 37, wherein said cap comprises at least one of the following materials: metal, titanium, plastic, and ceramic appropriate for implantation in the human body.

45. The cap of claim 37, wherein said cap is at least in part resorbable.

46. The cap of claim 37, wherein said cap is formed of a porous material.

47. The cap of claim 37, in combination with a material adapted to inhibit scar formation.

48. The cap of claim 37, in combination with an antimicrobial material.

49. The cap of claim 37, in combination with a spinal implant having upper and lower portions adapted to move apart from one another to contact the vertebral bodies and an end with an opening configured to cooperatively receive at least a portion of said cap.

50. The cap of claim 49, wherein said upper and lower portions of said implant include at least one opening adapted to communicate with one of the adjacent vertebral bodies, said openings in said upper and lower portions being in communication with one another and adapted for permitting for the growth of bone from adjacent vertebral body to adjacent vertebral body through said implant.

51. The cap of claim 50, wherein said implant includes a hollow interior for holding bone growth promoting material, said hollow interior being in communication with at least one openings in each of said upper an lower portions.

52. The cap of claim 49, wherein said implant is in combination with a bone growth promoting material.

53. The cap of claim 52, wherein said bone growth promoting material is selected from one of bone, bone derived products, demineralized bone matrix, ossifying proteins, bone morphogenetic protein, hydroxyapatite, an genes coding for the production of bone.

54. The cap of claim 49, wherein said implant is treated with bone growth promoting substance.

55. The cap of claim 49, wherein said implant comprises at least one of the following materials: metal, titanium, plastic, and ceramic appropriate for implantation in the human body.

56. The cap of claim 49, wherein said implant is at least in part resorbable.

57. The cap of claim 49, wherein said implant is formed of a porous material.

58. The cap of claim 49, wherein said implant is in combination with a material adapted to inhibit scar formation.

59. The cap of claim 49, wherein said implant is in combination with an antimicrobial material.

60. An implant cap for preventing the over-expansion of an expandable spinal implant having upper and lower portions adapted to move apart from one another to contact adjacent upper and lower vertebral bodies, respectively, and an end having an opening configured to cooperatively receive at least a portion of said cap, each of the upper and lower portions proximate the end of the implant having a recess, said cap comprising:
 a head configured to cooperatively engage the end of the implant to at least in part cover the opening, said head having a top surface and a bottom surface opposite said top surface, said bottom surface having at least one protrusion adapted to cooperatively engage the recesses in the end of the implant to prevent the implant from expanding beyond a predetermined height by limiting movement of the upper and lower portions relative to one another; and
 a stem projecting from said bottom surface of said head, said stem being adapted for insertion into the opening of the implant.

61. The cap of claim 60, wherein said head is configured to cooperatively engage the end of the implant to completely cover the opening.

62. The cap of claim 60, wherein the implant has a plurality of bone screw holes, said bottom surface of said head being configured to cover at least a portion of one of the bone screw holes when said cap is engaged to the implant.

63. The cap of claim 62, wherein said bottom surface of said head is configured to cover a portion of more than one of the bone screw holes when said cap is engaged to the implant.

64. The cap of claim 62, wherein said head is configured to allow the insertion of a bone screw into the implant after said cap is engaged with the implant.

65. The cap of claim 62, wherein said head has a perimeter that is configured to permit the insertion of a bone screw into one of the bone screw holes after said cap is engaged with the implant, said head being movable to cover at least a portion of the bone screw after the bone screw is inserted in one of the bone screw holes.

66. The cap of claim 60, wherein said cap is treated with a bone growth promoting substance.

67. The cap of claim 60, wherein said cap comprises at least one of the following materials: metal, titanium, plastic, and ceramic appropriate for implantation in the human body.

68. The cap of claim 60, wherein said cap is at least in part resorbable.

69. The cap of claim 60, wherein said cap is formed of a porous material.

70. The cap of claim 60, in combination with a material adapted to inhibit scar formation.

71. The cap of claim 60, in combination with an antimicrobial material.

72. The cap of claim 60, in combination with a spinal implant having upper and lower portions adapted to move apart from one another to contact the vertebral bodies and an end with an opening configured to cooperatively receive at least a portion of said cap.

73. The cap of claim 72, wherein said upper and lower portions of said implant include at least one opening adapted to communicate with one of the adjacent vertebral bodies, said openings in said upper and lower portions being in communication with one another and adapted for permitting for the growth of bone from adjacent vertebral body to adjacent vertebral body through said implant.

74. The cap of claim 73, wherein implant includes a hollow interior for holding bone growth promoting material, said hollow interior being communication with at least one openings in each of said upper an lower portions.

75. The cap of claim 72, wherein said implant is in combination with a bone growth promoting material.

76. The cap of claim 75, wherein said bone growth promoting material is selected from one of bone, bone derived products, demineralized bone matrix, ossifying proteins, bone morphogenetic protein, hydroxyapatite, an genes coding for the production of bone.

77. The cap of claim 72, wherein said implant is treated with bone growth promoting substance.

78. The cap of claim 72, wherein said implant comprises at least one of the following materials: metal, titanium, plastic, and ceramic appropriate for implantation in the human body.

79. The cap of claim 72, wherein said implant is at least in part resorbable.

80. The cap of claim 72, wherein said implant is formed of a porous material.

81. The cap of claim 72, wherein said implant is in combination with a material adapted to inhibit scar formation.

82. The cap of claim 72, wherein said implant is in combination with an antimicrobial material.

83. A screw lock for locking a plurality of bone screws to a spinal implant, the implant having upper and lower portions adapted to move apart from one another to contact adjacent upper and lower vertebral bodies, respectively, the implant having a trailing end with a plurality of bone screw holes and an opening adapted to cooperatively receive at least a portion of said lock, said lock comprising:

a head having a top surface and a bottom surface opposite said top surface, said bottom surface being adapted to cover at least a portion of the bone screw holes when the implant is in an expanded position; and a stem projecting from said bottom surface of said head, said stem being adapted for insertion into the opening of the trailing end of the implant to move apart the upper and lower portions to an increased height of the implant upon rotation of said stem from an insertion position to a deployed position, said stem having a non-circular cross section transverse to the longitudinal axis of said stem.

84. The lock of claim 83, wherein said head is configured to cooperatively engage the trailing end of implant to completely cover the opening.

85. The lock of claim 83, wherein said stem has a rectangular cross section along at least a portion of the length of said stem.

86. The lock of claim 83, wherein said stem has a distal end adapted to cooperatively engage one of the upper and lower portions to lock said lock to the implant while the implant is in an expanded position.

87. The lock of claim 86, wherein said distal end of said stem has projections to cooperatively engage the upper and lower portions of the implant.

88. The lock of claim 83, wherein said bottom surface of said head has at least one recess and each of the upper and lower portions proximate the end of the implant has at least one protrusion, each recess being adapted to engage with at least one of the protrusions to prevent the implant from expanding beyond a predetermined height when the implant is expanded.

89. The lock of claim 83, wherein said lock is treated with a bone growth promoting substance.

90. The lock of claim 83, wherein said lock comprises at least one of the following materials: metal, titanium, plastic, and ceramic appropriate for implantation in the human body.

91. The lock of claim 83, wherein said lock is at least in part resorbable.

92. The lock of claim 83, wherein said lock is formed of a porous material.

93. The lock of claim 83, in combination with a material adapted to inhibit scar formation.

94. The lock of claim 83, in combination with an antimicrobial material.

95. The lock of claim 83, in combination with a spinal implant having upper and lower portions adapted to move apart from one another contact the vertebral bodies and a trailing end with an opening configured to cooperatively receive at least a portion of said lock.

96. The lock of claim 95, wherein said upper and lower portion of said implant include at least one opening adapted to communicate with one of the adjacent vertebral bodies, said openings in said upper and lower portions being in communication with one another and adapted for permitting for the growth of bone from adjacent vertebral body to adjacent vertebral body through said implant.

97. The lock of claim 96, wherein said implant includes a hollow interior for holding bone growth promoting material, said hollow interior being in communication with at least one openings in each of said upper a lower portions.

98. The lock of claim 95, wherein said implant is in combination with a bone growth promoting material.

99. The lock of claim 98, wherein said bone growth promotion material is selected from one of bone, bone derived products, demineralized bone matrix, ossifying proteins, bone morphogenetic protein, hydroxyapatite, and genes coding for the production of bone.

100. The lock of claim 95, wherein said implant is treated with a bone growth promoting substance.

101. The lock of claim 95, wherein said implant comprises at least one of the following materials: metal, titanium, plastic, and ceramic appropriate for implantation in the human body.

102. The lock of claim 95, wherein said implant is at least in part resorbable.

103. The lock of claim 95, wherein said implant is formed of a porous material.

104. The lock of claim 95, wherein said implant is in combination with a material adapted to inhibit scar formation.

105. The lock of claim 95, wherein said implant is in combination with an antimicrobial material.

106. A method for engaging an end cap having a stem to an expandable spinal implant having an end, the method comprising the steps of:

inserting the stem of the end cap into the end of the implant;

rotating the stem of the end cap to expand the height of the implant; and using a portion of the end cap to prevent the implant from expanding beyond a predetermined height.

107. The method of claim 106, wherein the step of rotating the stem includes rotating the stem less than one full turn to expand the implant to an increased maximum implant height.

108. The method of claim 106, wherein the step of rotating the stem includes rotating the stem approximately 90 degrees.

109. The method of claim 106, wherein the step of rotating the stem includes rotating a stem having no threads.

110. The method of claim 106, wherein the step of using a portion of the end cap includes receiving into at least one recess on the end cap at least one protrusion on the end of the implant.

111. The method of claim 106, wherein the step of using a portion of the end cap includes engaging at least one protrusion on the end cap into at least one recess on the end of the implant.

112. The method of claim 106, further comprising the step of locking the cap to the implant.

113. The method of claim 106, further comprising the step of locking the implant in an expanded position.

114. The method of claim 106, wherein the implant has a plurality of bone screw holes, further comprising the step of covering at least a portion of the bone screw holes with at least a portion of the end cap.

115. The method of claim 114, further comprising the step of inserting at least one bone screw in the implant after the stem of the end cap inserted into the end of the implant.

116. The method of claim 106, wherein the end of the implant includes an opening leading to an interior hollow having a bone growth promoting material therein, further comprising the step of covering at least a portion of the opening with the end cap.

\* \* \* \* \*

UNITED STATES PATENT AND TRADEMARK OFFICE
CERTIFICATE OF CORRECTION

PATENT NO.      : 6,849,093 B2
DATED           : February 1, 2005
INVENTOR(S)     : Gary K. Michelson It is certified that error appears in the above-identified patent and that said Letters Patent is hereby corrected as shown below:

Column 12,
Line 24, change "heed" to -- head --;
Line 48, change "surface" to -- surfaces --;
Line 66, change "as" to -- has --.

Column 13,
Line 51, change "portions a" to -- portions --;
Line 60, change "upper an" to -- upper and --.

Column 14,
Line 7, change "lest" to -- least --;
Line 20, change "an nd" to -- an end --

Column 15,
Lines 16 and 22, change "an" to -- and --.

Column 16,
Line 35, change "wherein" to -- wherein said --;
Lines 38 and 44, change "an" to -- and --;
Line 47, change "with" to -- with a --.

Column 17,
Line 14, change "of" to -- of the --;
Line 48, change "another" to -- another to --;
Line 61, change "upper a" to -- upper and --.

UNITED STATES PATENT AND TRADEMARK OFFICE
CERTIFICATE OF CORRECTION

PATENT NO.    : 6,849,093 B2
DATED         : February 1, 2005
INVENTOR(S)   : Gary K. Michelson It is certified that error appears in the above-identified patent and that said Letters Patent is hereby corrected as shown below:

Column 18,
Line 57, change "cap" to -- cap is --.

Signed and Sealed this

Third Day of May, 2005

JON W. DUDAS
*Director of the United States Patent and Trademark Office*